United States Patent
Witte

(10) Patent No.: US 8,822,725 B2
(45) Date of Patent: Sep. 2, 2014

(54) PROCESS FOR THE PREPARATION OF AN AQUEOUS COLLOIDAL PRECIOUS METAL SUSPENSION

(75) Inventor: Peter Theodorus Witte, Utrecht (NL)

(73) Assignee: BASF Corporation, Florham Park, NJ (US)

( * ) Notice: Subject to any disclaimer, the term of this patent is extended or adjusted under 35 U.S.C. 154(b) by 817 days.

(21) Appl. No.: 12/863,508

(22) PCT Filed: Jan. 27, 2009

(86) PCT No.: PCT/NL2009/050039
§ 371 (c)(1),
(2), (4) Date: Oct. 6, 2010

(87) PCT Pub. No.: WO2009/096783
PCT Pub. Date: Aug. 6, 2009

(65) Prior Publication Data
US 2011/0015451 A1    Jan. 20, 2011

(30) Foreign Application Priority Data

Jan. 28, 2008 (EP) .................................... 08150726

(51) Int. Cl.
C07C 211/00 (2006.01)
C07C 221/00 (2006.01)
C07C 223/00 (2006.01)
C07C 225/00 (2006.01)

(52) U.S. Cl.
USPC ....................................................... 564/291

(58) Field of Classification Search
None
See application file for complete search history.

(56) References Cited

U.S. PATENT DOCUMENTS

| 5,817,592 A | 10/1998 | Heinke et al. |
| 6,090,746 A * | 7/2000 | Bonnemann et al. ......... 502/325 |
| 2003/0109589 A1 | 6/2003 | Chane-Ching |

FOREIGN PATENT DOCUMENTS

| WO | WO 93/16157 | * 8/1993 |
| WO | 9617685 | 6/1996 |

OTHER PUBLICATIONS

Kim et al., "Facile One-Pot Synthesis of Gold Nanoparticles Using Alcohol Ionic Liquids", Journal of Materials Chemistry, vol. 16, pp. 1315-1317; 2006.
Aslam et al., "Novel One-Step Synthesis of Amine-Stabilized Aqueous Colloidal Gold Nanoparticles", Journal of Materials Chemistry, vol. 14, pp. 1795-1797; 2004.
Bonnemann et al., "Surfactant Stabilized Palladium Colloids as Precursors for cis-Selective Alkyne-hydrogenation Catalysts", Applied Organometallic Chemistry, vol. 11, pp. 783-796; 1997.
Chen et al., "Effects of Alkylated Polyethylenimines on the Formation of Gold Nanoplates", Langmuir, vol. 23, pp. 6801-6806; 2007.

* cited by examiner

*Primary Examiner* — Fereydoun G Sajjadi
*Assistant Examiner* — Jennifer C Sawyer
(74) *Attorney, Agent, or Firm* — Hoffmann & Baron, LLP

(57) ABSTRACT

The invention is directed to a process for the preparation of an aqueous colloidal precious metal suspension, which process comprises reducing a precious metal salt in aqueous solution using a functionalized, water soluble quaternary ammonium salt in the absence of organic solvents, to form elementary nanoparticles.

10 Claims, No Drawings

PROCESS FOR THE PREPARATION OF AN AQUEOUS COLLOIDAL PRECIOUS METAL SUSPENSION

This application is the U.S. National Phase of, and Applicant claims priority from, International Patent Application Number PCT/NL2009/050039 filed 27 Jan. 2009 and European Patent Application Number 08150726.1 filed 28 Jan. 2008, each of which are incorporated herein by reference.

BACKGROUND OF THE INVENTION

The invention is directed to a process for the preparation of an aqueous colloidal precious metal suspension, as well as to the preparation of a supported precious metal catalyst, using the said suspension.

Metal colloids, more in particular precious metal colloids, are used as starting materials for the preparation of supported (precious) metal catalysts. Precious metal colloids are usually prepared by reducing a precious metal ion in an organic solvent, mostly at elevated temperature.

The most often used method is reduction using an alcohol. This can either be a low boiling alcohol, such as the $C_1$ to $C_4$ alcohols, more in particular methanol, or high boiling solvents containing a hydroxyl group, such as ethylene glycol, or diethylene glycol mono-n-butyl ether. When low boiling alcohols are used, a separate stabilizer is added. The metal salt (ion) is mixed with the stabilizer in an alcoholic solution and refluxed for several hours. The high boiling materials require very high temperatures and often a protective atmosphere (nitrogen) and/or a high pH.

There are some methods which do not require the use of organic solvents or additives, such as the use of citrate as reductant and stabilizer. The lower limit of the particle size is, however, about 5 nm. It is difficult, or even impossible to produce nanoparticles of lower particle size.

The use of borate as reducing agent has the disadvantage of high pH and a very cumbersome feed method, if one needs a narrow particle size distribution. This method is already difficult at laboratory scale, but impossible to operate at industrial scale. The same applies to the use of 3-acetic acid thiophene as reducing and stabilizing agent.

SUMMARY OF THE INVENTION

Accordingly it is an object of the present invention to provide a process that has one or more of the following advantages over the prior art:
- absence of organic solvent;
- mild conditions of pH and temperature
- short reaction times
- no specific requirements as to protective atmosphere
- no special mixing and stirring conditions
- broad range of particle sizes that can be produced; even below 5 nm
- use of environmentally safe reactants.

An important use of the colloidal nanoparticles resides in the preparation of supported precious metal catalysts. Traditional methods for the preparation thereof generally yield catalysts that have small metal crystallites, but show a rather broad size distribution. It would be useful to have a process wherein the crystallite size distribution of the nanoparticles is rather narrow, thereby enabling the production of catalysts having a narrow crystallite size distribution.

DETAILED DESCRIPTION OF THE INVENTION

The present invention encompasses in a first embodiment a process for the preparation of an aqueous colloidal precious metal suspension, which process comprises reducing a precious metal salt in aqueous solution using a functionalised, water soluble quaternary ammonium salt in the absence of organic solvents, to form elementary nanoparticles.

An essential element of the process of the present invention resides in the use of the specific quaternary ammonium salt, namely a functionalised quaternary ammonium salt. In this respect the functionalisation comprises the presence of at least one reducing group, such as —$CH_2OH$ or cyclohexenyl, preferably in combination with at least one bulky group selected from the group of $C_6^+$-alkyl, cycloalkyl, aralkyl, alkaryl or aryl groups. In addition the quaternary ammonium salt can be chiral, such as a quaternised cinchonine or cinchonidine.

Preferred quaternary ammonium salts to be used in the process of the present invention are of the formula I:

$$RR'R''\text{—}N^+\text{—}CH_2CH_2OHX^-  \qquad \text{Formula I}$$

wherein R, R', and R" are independently of each other $C_1$-alkyl and higher and X is Cl, Br, $H_2PO_4$, $NO_3$, $SO_4$, etc. Preferably, R and R' are $C_1$-alkyl, and R" is $C_6$- and higher, more preferred $C_{16}$-alkyl.

The particle size of the elementary nanoparticles that are obtained by the process of the present invention is between 1 and 50, preferably between 1 and 10 nm.

The precious metal is selected from the group of platinum, palladium, iridium, rhodium, ruthenium, rhenium, silver, gold and combinations thereof, preferably palladium. Preferably a palladium salt is used, more specifically $Na_2PdCl_4$.

The process of the invention is very simple, as it suffices to combine the precious metal salt and the quaternary ammonium compound in an aqueous system, for example by mixing aqueous solutions of respectively the quaternary ammonium compound and the precious metal salt at a suitable temperature. Suitable temperatures are mainly determined by the reaction rate and the requirement that the compounds remain dissolved in a liquid system. Suitable temperatures for the solutions and the reaction mixture are between room temperature (20° C.) and near boiling point (95° C.).

According to a second embodiment the colloidal suspension may be used as catalytic material or for the preparation thereof.

According to a third embodiment of the invention, the colloidal suspension is used to produce supported precious metal catalysts. This process comprises preparing an aqueous colloidal precious metal suspension in accordance with the above process according to the invention, followed by contacting the suspension with a support material and recovering the precious metal catalyst or catalyst precursor by filtration and washing, optionally after addition of an aqueous alkaline solution (NaOH and the like) or ethanol.

The support is selected from the group of oxidic supports, such as silica, alumina, zirconia, titanium oxide and zinc-oxide, silicates, aluminates and active carbon. The amount of precious metal, calculated on the weight of the final catalyst is between 0.01 and 10 wt. %, preferably between 0.05 and 5 wt. % of the catalyst. The support may be in powder form, in the form of shaped particles, such as extrudates, or in the form of a structured material, such as a monolith.

The colloidal suspension produced in accordance with the process of the first embodiment of the invention as well as the heterogeneous catalyst produced in accordance with the process of this third embodiment of the invention may be used generally for all reactions for which precious metal catalysts are suitable. Examples are the usual hydrogenation reactions, such as hydrogenation itself, hydro-isomerisation, hydrodesulfurisation and hydro-dewaxing. The catalyst may also have been used in dehydrogenation reactions, such as catalytic reforming.

More in particular the catalyst is suitable for the production of 3-hexenol, which process comprises reducing 3-hexyn-1-ol in the presence of a catalyst as produced in accordance with the process above.

This process may conveniently be carried out in slurry phase or in a fixed bed in an organic solvent and the presence of hydrogen, either in a three phase system or in a two phase system, where the hydrogen is dissolved in the organic solvent. Preferred conditions for a slurry phase reaction are the use of an alkanol, such as hydrous ethanol as solvent, in the presence of 1 to 20 bar of gaseous hydrogen at a temperature between room temperature and about 75° C.

EXAMPLES

Example 1

Preparation of a Colloidal Suspension of Palladium

A solution of 15 g hexadecyl(2-hydroxyethyl)dimethylammonium dihydrogen phosphate in 1 L water is heated to 60° C. A solution of 0.75 g Pd (as $Na_2PdCl_4$) in 10 mL water is added in 3 minutes under vigorous stirring. The mixture is heated to 85° C. and stirred at this temperature for 2 hours. The heating is stopped and the colloidal suspension, thus obtained, is stirred for an additional hour, during which it cools down to 40° C.

Example 2

Preparation of Supported Palladium Catalyst

A slurry of 75 g carbon powder in 750 mL water is vigorously stirred for an hour at room temperature. The colloidal suspension obtained according to Example 1, containing 0.75 g Pd in 1 L water is added in 40 minutes. The mixture is stirred for an additional 45 minutes. The pH of the mixture is adjusted from 2.4 to 9.3 by addition of a 10% NaOH solution in 28 minutes. The mixture is stirred an additional 30 minutes, while the pH is kept between 9.0 and 9.3 by addition of 10% NaOH. The solid supported catalyst is filtered off and washed with water until the filtrate is chlorine-free according to a precipitation test with $AgNO_3$.

Example 3

Hydrogenation of 3-hexyn-1-ol Using a Supported Palladium Catalyst

A 250 mL stainless steel autoclave is charged with 500 mg of the catalyst produced according to Example 2 (1% Pd/C (dry weight)), 100 mL 96% ethanol, and 10 mL 3-hexyn-1-ol. The autoclave is closed and the mixture is heated to 30° C. with stirring. The stirring is stopped, and the air is replaced by flushing hydrogen over the mixture. After flushing the autoclave is pressurised with 3 bars of hydrogen. The stirring is resumed (1500 rpm) and the hydrogen consumption is recorded. After 2.0 L hydrogen is consumed the stirring is stopped, the hydrogen is vented off, and the autoclave is opened. Conversion and selectivity are determined by GC measurement of the crude reaction mixture. Conversion: 97%. Selectivity: >99% 3-hexenol of which 95% is the cis-isomer.

The invention claimed is:

1. Process for the preparation of an aqueous colloidal precious metal suspension, which process comprises reducing a precious metal salt in aqueous solution, wherein the reducing agent consists of a functionalised, water soluble quaternary ammonium salt, wherein the process takes place in the absence of organic solvents, wherein elementary nanoparticles are formed.

2. Process according to claim 1, wherein the functionalised, water soluble quaternary ammonium salt has a hydroxyl functionality.

3. Process according to claim 1, wherein the functionalised, water soluble quaternary ammonium salt has the formula:

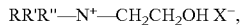

$$RR'R''—N^+—CH_2CH_2OH\ X^-,$$

wherein R, R' and R" are independently of each other C1-alkyl and higher and X is Cl, Br, $H_2PO_4$, $NO_3$, or $SO_4$.

4. Process according to claim 1, wherein the precious metal is selected from the group of platinum, palladium, iridium, rhodium, ruthenium, rhenium, silver, gold and combinations thereof.

5. Process according to claim 4, wherein the precious metal salt is $Na_2PdCl_4$.

6. Process according to claim 1, wherein the particle size of the elementary nanoparticles is between 1 and 50 nm.

7. Process according to claim 1, wherein the quaternary ammonium salt is a quaternary ammonium phosphate.

8. Process according to claim 1, wherein the amount of precious metal is between 0.01 and 10 wt. % of the catalyst.

9. Process according to claim 1, wherein the particle size of the elementary nanoparticles is between 1 and 10 nm.

10. Process according to claim 1, wherein the amount of precious metal is between 0.5 and 5 wt. % of the catalyst.

* * * * *